(12) United States Patent
Chaudhry

(10) Patent No.: US 10,238,104 B2
(45) Date of Patent: Mar. 26, 2019

(54) MULTIFUNCTIONAL NUTRITIONAL ADJUVANT CHEMICAL COMPOSITION FOR USE IN AGRICULTURE

(71) Applicant: Suunil Sudhakar Chaudhry, Jalgaon (IN)

(72) Inventor: Suunil Sudhakar Chaudhry, Jalgaon (IN)

(73) Assignee: Suunil Sudhakar Chaudhry, Jalgaon (IN)

( * ) Notice: Subject to any disclaimer, the term of this patent is extended or adjusted under 35 U.S.C. 154(b) by 0 days.

(21) Appl. No.: 15/022,865

(22) PCT Filed: Nov. 21, 2013

(86) PCT No.: PCT/IN2013/000709
§ 371 (c)(1),
(2) Date: Mar. 17, 2016

(87) PCT Pub. No.: WO2015/040627
PCT Pub. Date: Mar. 26, 2015

(65) Prior Publication Data
US 2016/0205927 A1   Jul. 21, 2016

(30) Foreign Application Priority Data
Sep. 19, 2013   (IN) .......................... 3028/MUM/2013

(51) Int. Cl.
| | |
|---|---|
| *A01N 25/30* | (2006.01) |
| *A01N 25/02* | (2006.01) |
| *C05F 11/00* | (2006.01) |
| *C05B 17/00* | (2006.01) |
| *A01N 25/00* | (2006.01) |

(52) U.S. Cl.
CPC ............ *A01N 25/30* (2013.01); *A01N 25/00* (2013.01); *A01N 25/02* (2013.01); *C05B 17/00* (2013.01); *C05F 11/00* (2013.01); *Y02E 50/343* (2013.01); *Y02W 30/47* (2015.05)

(58) Field of Classification Search
CPC ........ A01N 25/30; A01N 25/02; A01N 25/00; C05F 11/00; C05B 17/00
See application file for complete search history.

(56) References Cited

U.S. PATENT DOCUMENTS

| | | | |
|---|---|---|---|
| 4,684,695 A * | 8/1987 | Oshima | C08G 63/918 525/36 |
| 5,278,132 A | 1/1994 | Fisher et al. | |
| 6,312,493 B1 * | 11/2001 | Eltink | C05D 9/02 71/27 |
| 2010/0120619 A1 | 5/2010 | Greyling | |
| 2012/0103042 A1 * | 5/2012 | Sanders | C05B 7/00 71/28 |
| 2012/0157317 A1 | 6/2012 | Tanaka et al. | |
| 2013/0192322 A1 * | 8/2013 | Miller | C05B 15/00 71/23 |

FOREIGN PATENT DOCUMENTS

| | | | |
|---|---|---|---|
| CN | 1070794 | * | 4/1993 |
| CN | 1372796 A | | 10/2002 |
| WO | 99/25189 | | 5/1999 |
| WO | 2005/018334 A1 | | 3/2005 |
| WO | 2008/035237 A2 | | 3/2008 |

OTHER PUBLICATIONS

CN 1070794, English, machine translation.*

* cited by examiner

*Primary Examiner* — Mina Haghighatian
(74) *Attorney, Agent, or Firm* — Kramer Amado, P.C.

(57) ABSTRACT

The invention discloses herein a multifunctional nutritional adjuvant chemical composition for use in agriculture with water comprises pH modifying complex matrix, pH indicators, surfactants, penetrating agents, auxiliary chemicals and solvent; having multiple uses in agriculture such as pH corrector, auto pH indicator, wetting agent adjuvant, plants immune system activator, plant defense mechanism enhancer, nutrient supplement and plant growth hormone provider. The invention further discloses the process for preparation of said multifunctional nutritional adjuvant chemical composition.

21 Claims, No Drawings

MULTIFUNCTIONAL NUTRITIONAL ADJUVANT CHEMICAL COMPOSITION FOR USE IN AGRICULTURE

TECHNICAL FIELD OF THE INVENTION

The present invention relates to a multifunctional nutritional adjuvant chemical composition used in agriculture having multiple benefits that reduces the usage of agrochemicals by effectively increasing their efficiency. The invention further relates to the process for preparation of said multifunctional nutritional adjuvant chemical composition.

BACKGROUND AND PRIOR ART OF THE INVENTION

Water is the only effective and economical medium available for application of various agrochemicals in order to reduce the pests or kill the weeds or effectively supply nutrients for plants development.

The water used in agriculture is mainly sourced from borewell, open well, dam or river or water streams. The ground water used for agriculture purpose such as spraying various pesticide, weedicide, herbicide, insecticide, pesticide and fungicide is generally hard water having pH >7 because of the hardness causing bicarbonate, carbonate salts of calcium, magnesium and sodium present in the ground water.

It is well known that if one washes the clothes in such hard water clothes are not washed properly and quantity of soap required is more. This is due to the fact that in hard water efficiency of soap is affected and reduced. Due to hardness causing salts, some quantity of soap is hydrolyzed which reduces the efficacy of the washing soap.

Similarly, quality of water used in spray tanks can also affect the efficacy of herbicide or pesticide. Water is the primary carrier for herbicide applications. In fact, it usually makes up over 99% of the spray solution. The chemistry of water added to the spray tank greatly impacts herbicide effectiveness. In the same manner efficiency of applied agrochemicals is also reduced, if one uses the hard water for application of agrochemicals in plants.

Hard water contains high levels of Calcium (Ca), Magnesium (Mg), Sodium (Na) or Iron (Fe). Ca, Mg, Na, and Fe cations are positively charged ions attach to negatively charged pesticide, herbicide, insecticide molecules and due to this reaction often cations make pesticides, herbicides, fungicide, Plant Growth Regulator (PGR) less effective or ineffective.

High pH and hard water act together to reduce effectiveness of agrochemical, pesticide and herbicide. High pH causes more of the pesticide, agrochemical to dissociate while high concentrations of cations bind with the dissociated pesticide, agrochemical to reduce its effectiveness.

If the concentration of all the cations Ca, Mg, Na, and Fe in water exceeds 500 ppm then the water used for pesticide mixing will render the pesticide/agrochemical less effective and the treatment of water is necessary in order to achieve better performance of the herbicide/pesticide/agrochemical or applied agrochemical.

Similarly, if the alkalinity [Alkalinity refers to carbonate $((CO_3)_2-)$ and bicarbonate $(HCO_3-)$ levels in water] of water exceeds beyond certain value, it contains high bicarbonates and applying pesticide or herbicide in such water will render the herbicide less effective and the treatment of water is necessary in order to achieve better performance of the herbicide or applied agrochemical.

Further, due to the seasonal changes, vicinity of mineral deposits, the hardness and the alkalinity of the ground water changes. Research shows that the "half life" of the chemical varies with pH. Half Life means the time it takes for 50% of the product breakdown (hydrolyze) in water. Each half life that passes reduces the concentration of that agrochemical by 50% i.e. 100%, 50%, 25%, 12.5%, 6.25% and the like. For e.g. products like cypermethrin, glyfosate, benomyl, GA hydrolyze fast in alkaline hard water. Thus, the hard and alkaline water reduces the efficiency of pesticide, insecticide, herbicide, fungicide, PGR, micronutrients, fertilizers and other agrochemicals.

Agricultural chemicals such as pesticides, herbicides, fungicides, PGR, fertilizers, micronutrients are typically applied on plants and soil as an aqueous solution. Many of these agrochemicals have an activity that varies with pH of the solution. Many of these products are sensitive to alkaline waters or acidic waters. Many agrochemicals have optimum activity in slightly acidic pH range of about 4-6, whereas, herbicide like glyfosate functions well at pH=3.5.

Therefore, it is necessary to adjust the pH of the water before the addition of agrochemical into the water to prepare the solution for spraying. The pH correction can be done by acids or alkali and the pH meter or pH paper is required to check the adjustment in the pH made of water using pH modifiers.

Generally, it is time consuming and requires sophisticated delicate pH meter which needs protection from shocks and contact of electronic parts with water. Sensitive pH paper may degrade and be unuseful if it comes in contact with water, high humidity or atmospheric moisture during rainy season. Sometimes determination of pH may show some error because the pH meter needs to be calibrated frequently with different range pH solutions, so it becomes quiet cumbersome in the field to check the pH of the water using above methods. It is required to avoid such problems in the field during the preparation of the solution of pesticide, insecticide, herbicide, fungicide, PGR, micronutrients, fertilizers and other agrochemicals.

U.S. Pat. No. 5,278,132 claims the concentrate which is a mixture of pH modifying agent and a PH indicator which are selected so that the concentrate when diluted in water it adjusts the pH of the water and indicates the pH of water. The pH modifying agents used as acetic acid, orthophosphoric acid, citric acid along with buffers such as ammonia, MAP, MPP, Potassium hydrogen phthalate, sodium acetate. The pH indicator used is member selected from methyl red, recorcin blue, 2-5 di-nitrophenol and chlorophenol red.

PCT Publication No. 2008/035237 discloses a concentrate which includes an adjuvant, a first pH indicator, and a second pH indicator. The pH lower limit of the first pH indicator corresponds to the pH upper limit of the second indicator. Preferably, at this pH, the color of the indicators is the same, and is preferably a light color (e.g. yellow).

PCT Publication No. 2005/018334 discloses the pH indicator for use with Agricultural Compounds. Said publication discloses new class of pH indicators which are mainly naturally occurring substances from grape skin, cabbage and lecithin as adjuvant emulsifier. This publication uses orthophosphoric esters as pH modifying agents.

US Publication No. 2010/0120619 describes the concentration for dilution with water in the preparation of agricultural compositions and its application on crops and animals. The concentrate indicates different colors of spray water at different pH levels. The color changes is as Blue at to yellow at pH about 5.0-5.5 indicated by bromocresol green indicator and color change of yellow to orange red at 3.0-3.5 as indicated by methyl yellow.

Two groups of pH indicators are used in U.S. '619, one group of pH indicator is selected such that intermediate color that is overlapping color of lower end of one pH indicator and the higher end of the other group of pH indicator is same.

The pH indicators discussed are—

For color change of Green to Yellow to orange/red are:—
Group 1:—bromocresol green (Blue at pH 7.4 and yellow at pH 5.6),
bromoxylenol blue (blue at pH 5.6 and yellow at pH 4.0),
Group 2:—Methyl yellow (yellow at pH 4.5 and red at pH 3.2),
methyl orange (yellow at pH 4.5 and red at pH 3.2),
Naphtyl Red (yellow at pH 5.0 and red at pH 3.7).

For color change of purple to yellow to orange/red:—
Group 3:—Bromophenol red (purple at pH 7.0 and yellow at pH 5.2),
chlorophenol red (purple-red at pH 6.6 and yellow at pH 5.2),
alizarin red (red at pH 6 and yellow at pH 4.4),
cochineal (purple at pH 6.2 and yellow at pH 4.8),
Group 4:—Methyl yellow (yellow at pH 4.5 and red at pH 3.2),
methyl orange (yellow at pH 4.5 and red at pH 3.2),
Naphtyl Red (yellow at pH 5.0 and red at pH 3.7).

For acidic sensitive agrochemicals fungicides alkaline pH indicators from following group are used.
Group 5:—Xylenol blue (blue at pH 9.5 and yellow at pH 8.0)
O-cresol red (red at pH 8.8 and yellow at pH 7.2)
M cresol purple (purple at pH 9.2 and yellow at pH 7.6)
1-Naptholbenzene (green at pH 9.8 and yellow at pH 8.4).
Group 6:—Neutral red (yellow at pH 8.0 and red at pH 6.8)

Further, U.S. '619 uses orthophosphric acid, acetic acid, nitric acid, hydrochloric acid, sulfuric acid and formic acid as pH modifying agents. The concentrate disclosed gives benefit to have pH indication at 2 different pH levels by showing 2 different colors. The color change at pH 5.5 i.e. lower end is yellow using various pH indicators. Sometime in the field, when the water is not clear or become dirty due to dirt in rainy season then the color of the water become turbid and it becomes difficult to recognize of yellow color imparted to water by pH indicator.

US Patent Publication No. 2012/0157317 discloses a concentrate in which the pH indicator is triarylmethane and the adjuvant is a carbohydrate (organic) acid for pH modification. The invention provides composition in concentrated form for dilution with water in the preparation of agricultural composition for application to crops, soil or animals. The pH modifying agent used is carbohydrate acid selected from glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, eruythronic acid, threonic acid, tartaric acid and any composition thereof. It also mentioned about the other acids such as acetic acid, orthophisphoric acid, citric acid, glutaric acid, glycolic acid, lactic acid, malonic acid, oxalic acid, phthalic acid, succinic acid, phosphorous acid, amino-tris(methylenephosphonic) acids and etidronic acid. The said patent uses carbohydrate acid for pH modification.

PCT Publication No. WO9925189 claims a concentrate for enhancing the activity of an agricultural chemical comprising pH modifying agents and water conditioning agents; along with a pH indicator for coloring water; the pH indicator producing a colour change in water at a pH at which the agricultural chemical has an acceptable agricultural activity. The pH modifying agent is selected from the group comprising acids, alkalis, buffers and salts for controlling or modifying the pH of water and the pH indicator is selected from the group comprising methyl red, bromocresol purple, and bromocresol green.

Abstract of Chinese Patent Publication No. CN1372796 describes a concentrated chemical for agricultural purpose, such as for crops, soil or animals, can be diluted by water, and contains the chemical and pH value indicator able to dye water. It characterized by that the activity of said chemical changes with the pH value of water, so visually indicating the activity of said chemical according to the color of liquid.

Though, the above mentioned prior art patents/patent Publications teaches the use of pH modifying agent with pH indicator, however, the agriculture composition mentioned above does not offer any other benefits than pH adjustment and pH indication using pH indicators.

Therefore, there is a need in the art to provide a more effective composition in the field of agriculture, hence, the inventor of the present invention have come up with a multifunctional adjuvant chemical composition, which offers multiple benefits by acting in multiple ways and reduce the usage of agrochemicals by effectively increasing their efficiency about 25-35% by treating the water for its hardness causing salts which render the agrochemicals/pesticides less effective.

The multifunctional adjuvant chemical composition for use in agriculture to treat the water for its hardness by using pH correctors automatically allow the end user to know the pH of the corrected water by visual indication instead of taking the use of large cumbersome, difficult to handle pH meters and pH papers. The multifunctional chemical composition also has surface tension reducing property and thus enhances the coverage of applied agrochemical.

The additional features of the present composition is that, apart from treating the water for its hardness causing salts, it also acts to improve the immune system and defense mechanism of plant and supplies nutrient such as phosphite ion, nitrogen in the form amino acids, hard water containing calcium and magnesium in the form of complexed phosphite salts and hormone in the form of pH indicator.

SUMMARY OF THE INVENTION

In accordance with the above, in an aspect, the present invention discloses a multifunctional nutritional adjuvant chemical composition comprises of pH modifying complex matrix, pH indicators, Surfactants, Penetrating agents, Auxiliary chemicals and Solvent.

In another aspect, the multifunctional nutritional adjuvant chemical composition is diluted with water for preparing the agrochemical solution that contains agrochemical whose activity varies with the pH of water.

In another aspect, the multifunctional adjuvant chemical composition is prepared in various forms such as Liquid, Gel, Paste, Solid Powder, Granule, Tablet or Pellet.

In yet another aspect, the invention discloses the process for preparation of said multifunctional nutritional adjuvant chemical composition.

DETAILED DESCRIPTION OF THE INVENTION

The invention will now be described in detail in connection with certain preferred and optional embodiments, so that various aspects thereof may be more fully understood and appreciated.

In a preferred embodiment, the present invention discloses a multifunctional nutritional adjuvant chemical composition comprises of pH modifying complex matrix (pH correctors), pH indicators, Surfactants, wetting agents, Penetrating agents, auxiliary chemicals and solvent; having multiple uses in agriculture such as pH corrector, auto pH indicator, wetting agent adjuvant, plants immune system activator, plant defense mechanism enhancer and complexed nutrient supplement and growth hormone provider.

Accordingly, in another embodiment, pH modifying complex matrix of the present invention comprises organic, inorganic acids such as Maleic anhydride 15-25% by volume, Water to hydrolyze maleic anhydride into maleic acid, Itaconic acid 1-3% by volume, Phosphorous acid (H3PO3) 15-25% by volume, amino acids such as Glycine 4-6% by volume, Hydrolyzed Proteins 4-8% by volume, and Linear alkyl benzene sulfonic acid such as dodecyl benzene sulfonic acid 1-3% by volume.

The pH modifying complex matrix of the present invention comprises organic, inorganic acids and is present in an amount ranges from 45-55% by volume of the total composition, in liquid or paste form.

pH modifying complex matrix of the present invention act as a pH correctors/adjuster, plants immune system activator, provide Nutrient supplement and perform surfactant action.

The Maleic anhydride derived maleic acid and Itaconic acid acidifies the pH of water and complexes the hardness causing salts.

Phosphorous acid ($H_3PO_3$) acts as strong pH adjuster/corrector and simultaneously acts as plant's own immune system and defense system activator. Phosphite from phosphorous acid promotes the plants natural defense and induces the synthesis of phytoalexins in such a way that the plants resistance is strengthened against attacks from fungus or bacteria. The phosphite ion provides a prophylactic effect against fungus, strengthens the stem and the roots against attacks by fungus and other diseases and prevents rotting in conditions of high humidity.

Phosphorous acid ($H_3PO_3$) is useful to improve plants internal defense mechanism against fungal and microbial disease whereas phosphoric acid ($H_3PO_4$) can't do this additional work/job apart from acting as pH corrector.

Phosphites are highly mobile molecules, readily absorbed by both leaves and roots, and are translocated throughout the plant. Phosphorous acid triggers molecular reactions within the plant cell to exert its fungistatic effect through activating plants own immune system and defense mechanisms. Phosphonates alter the fungal wall and inhibits its further proliferation by suppressing the spore formation. In this way it controls the disease and its further spread. Therefore, phosphite molecule has dual mechanism of action—pH adjustment and increase fungal resistance. The phosphite induced phytoalexin accumulation in plant as the result of the reactions occurring at molecular level upon fungal infection.

Amino acids synthetic such as Glycine and hydrolyzed proteins containing L amino acids from natural vegetable or animal, microorganism origin sources such as soy or any other hydrolyzed proteins, Amino Acids sourced from natural origin products. Amino acids although weak acids are beneficial in complexing hardness causing salts of calcium, magnesium bicarbonate, carbonate in water. Hydrolyzed proteins and amino acids provides nutrient to plants. The amino acids and hydrolyzed proteins present in pH modifier complex matrix helps to transport the applied agrochemicals in plants because amino acids are natural transporters and acts as chelating agents and very helpful in improving the absorption of the products with which they are used.

By treating hard water, the complex products formed such as Calcium, Magnesium, Iron Amino Phosphite, that are soluble compounds, beneficial to plants by providing them with phosphite ion with amino acids, proteins which improve the plants health.

Additional pH modifier such as linear alkyl benzene sulfonic acid (dodecyl benzene sulfonic acid) is also employed in the present composition which acts as acidifier with surfactant action.

In another embodiment, the composition of present invention comprises pH indicators for coloring the solution and are selected from variety of pH indicators either natural or synthetic pH indicators such as combination of methyl red, para and ortho-nitrophenol sodium salts, methylene blue, congo red, Bromothymol Blue, Thymol Blue, Phenolphthalein, methyl orange, and xylene cyanol. Other coloring pH indicators used such as neutral red, napthyl red, bromocresol purle, bromo xylenol blue, bromocresol green, alizarin red, ortho cresol red, resazurin and 2-4 di nitro phenol.

There are some other pH indicators used in the present invention such as para and ortho nitrophenol having pH indicating range of 5 to 7 (at pH 7 it is yellow and at 5 pH it is colorless) which also act as plant growth hormone at low concentrations. They are also useful in increasing absorption of nutrients from soil, improved photosynthesis and better metabolism. This additional effect on increasing plant health, due to the use of pH indicator, is not available in the compositions discussed in the prior art.

The pH indicators used in the present invention are present in an amount of 0.8 to 3.0% by volume of the total composition.

In another embodiment, the composition of present invention comprises surfactant/wetting agents for reducing the surface tension of water includes Organo silicone based surfactant compound 3-6%, Sorbitan Mono oleate 2-4%, Sodium lauryl sulfate 2-4% and dioctylsulfosuccinate sodium salt 1-2%. The amount of surfactant/wetting agents used is 8-15% by volume of the total composition.

In another embodiment, the composition of present invention comprises Penetrating agents and Solvents for pH Indicators includes Propanol 2-4%, Methanol 2-4%, Ethylene Glycol/Propylene Glycol 3-6%. The amount of Penetrating agents and Solvents for pH Indicators used is 5-10% by volume of the total composition.

In another embodiment, the composition of present invention comprises auxiliary chemicals such as thickener, antifoaming agent, defoamers 0.1% w/v based on silicone/wax based defoamer, humectant 1-5% such as glycerin and stabilizer.

The thickeners are selected from Sodium CMC, Guar gum/Xanthan Gum and Polyacryl amide, present in an amount of 0.03 to 0.15% w/v of the total composition.

The solvent used in the composition of the present invention is universal solvent Water (Q.S.).

By adding the multifunctional adjuvant chemical composition of the present invention in the water, it helps the farmer/grower to understand the gradual change in pH of water from >7 to 6 to 5 to 4 to 3 due to visual change in color of water and farmer can clearly understand how the water quality and pH is changing by addition of the multifunctional chemical composition of the present invention.

In another preferred embodiment, the multifunctional nutritional adjuvant chemical composition of the present invention is prepared in various forms such as Liquid, Gel, Paste, Solid Powder, Granule, Tablet or Pellet in one pack or in twin pack.

The multifunctional nutritional adjuvant chemical composition of the present invention is prepared in ONE PACK system comprises pH modifying complex matrix (pH correctors), pH indicators, Surfactants/wetting agents, Penetrating agents, auxiliary chemicals and solvent.

In alternate embodiment, the multifunctional nutritional adjuvant chemical composition of the present invention is prepared in TWIN PACK system, which comprises of first pack containing pH modifier complex with surfactants and second pack containing pH indicators with solvents, penetrator, thickener and other auxiliary chemicals.

In another preferred embodiment, the present invention discloses the process for preparation of multifunctional nutritional adjuvant chemical composition of the present invention comprises of, a) hydrolyzing maleic anhydride into maleic acid by adding maleic anhydride into water followed by allowing it to hydrolyse by applying heat at 75-80° C. to form maleic acid;

b) adding itaconic acid, phosphorous acid, glycine and hydrolyzed proteins subsequently into the maleic acid solution of step (a) to obtain pH modifier matrix;

c) slowly adding surfactants/wetting agents, natural or artificial thickeners to the solution obtained in step (b) under stirring and maintaining the temp. at 65-75° C.;

d) preparing the pH indicator solution using penetrators and pH indicator solvents;

e) adding pH indicator solution of step (d) to the solution obtained in the step (c) and finally making the volume to 100% by volume using hot demineralised water to obtain the formulation;

f) optionally, drying the formulation of step (e) in vacuum or in spray dryer to form dry version of the final product followed by converting into granule or tablet or pellet form.

In another embodiment, the present invention discloses the method of improving Systemic Acquired Resistance (SAR), internal immune system and defense mechanism of the plant against fungal and microbial diseases that make plant strong by mixing multifunctional nutritional adjuvant chemical composition comprising pH modifying complex matrix (pH correctors), pH indicators, Surfactants/wetting agents, Penetrating agents, auxiliary chemicals and solvent, with hard water.

In another embodiment, the present invention discloses the method of providing nutrient supplement and growth hormone to plants by mixing multifunctional nutritional adjuvant chemical composition comprising pH modifying complex matrix (pH correctors), pH indicators, Surfactants/wetting agents, Penetrating agents, Auxiliary chemicals and solvent, with hard water.

In a further another embodiment, the present invention discloses the use of multifunctional nutritional adjuvant chemical composition of the present invention comprising pH modifying complex matrix (pH correctors), pH indicators, Surfactants/wetting agents, Penetrating agents, auxiliary chemicals and solvent; for improving the Systemic Acquired Resistance (SAR), internal immune system and defense mechanism of the plant against fungal and microbial diseases that make plant strong and providing nutrient supplement and growth hormone to plants.

The following example, which includes preferred embodiments, will serve to illustrate the practice of this invention, it being understood that the particulars shown are by way of example and for purpose of illustrative discussion of preferred embodiments of the invention.

Example 1: Using Screened Indicators

Color Change: Parrot Green at pH 6.2 and Purple at pH 4.5 to 4.80

|  | Ingredients | Amount/Range |
| --- | --- | --- |
| pH Modifier matrix | Maleic anhydride | 18 gm |
|  | Water to hydrolyze into maleic acid | 55 ml |
|  | Itaconic acid | 1 gm |
|  | Phosphorous acid H3PO3 | 20 gm |
|  | Glycine | 4 gm |
|  | Hydrolyzed Proteins | 5 gm |
|  | Linear alkyl benzene sulfonic acid/ dodecyl benzene sulfonic acid | 1 gm |
| Surfactant | Sodium Lauryl sulfate | 2 gm |
|  | Polysorbate Sorbitan monooleate | 2 gm |
|  | Organo Silicone surfactant | 6 gm |
|  | dioctylsulfosuccinate | 1 gm |
| Penetrator and Solvent for Indicator | Methanol/propanol/Ethylene Glycol/Propylene Glycol | 5-8 ml |
| pH Indicator | Methyl Red | 0.2 gm |
|  | Methylene Blue | 0.1 gm |
|  | Para nitro phenol | 0.5 gm |
| Thickener | Sodium CMC | 0.05 gm |
|  | Guar gum/Xanthan Gum | 0.05 gm |
|  | Polyacryl amide | 0.05 gm |
| Water | To make volume | 100 ml |

Step a: Hydrolyzing maleic anhydride into maleic acid by adding maleic anhydride into water and allowing it to hydrolyse by applying heat at 75-80° C. to form maleic acid then adding itaconic acid, phosphorous acid, glycine and hydrolyzed protein subsequently into this solution to make maleic itaconic phosphorous acid amino acid complex.

Step b: To above solution of pH modifier matrix, surfactants, wetting agents such as Organo silicone surfactant, Sorbitan monooleate, Sodium lauryl sulphate, dioctyl sulfosuccinate are added. Natural or artificial thickeners such as guar gum, sodium CMC, xanthum gum, polyacrylates, carbomers are added slowly under stirring maintaining a temp of 65-75° C.

Step c: Preparation of pH indicators solution—pH indicators solution is made separately in separate vessel using solvent for pH indicators and penetrators such as methanol and propanol and using penetrator from glycol series such as monoethylene glycol, propylene glycol by mixing thoroughly all the pH indictors mentioned in the composition.

Step d: Adding pH indicator solution containing penetrators and pH indicators solvents to the solution obtained in the step (b) and finally making the volume to 100% by volume using hot demineralised water to obtain the formulation.

Step e (Optional): The above formulation can also be dried in vacuum or in spray dryer to form dry version of the product and can be converted into granule or tablet form.

The composition of Example 1 when added into hard water having alkaline pH >7 e.g. pH 8.5, the hardness causing salts are complexed and the pH is reduced from 8.5 to 4.0. The color change is noted as Parrot Green at pH 6.2, Orange Red at 5.0, Purple at pH 4.0-4.2. This is suitable for most of the pesticides when the pH is required to be adjusted at 4.2 to 6.0.

Colour Change Noticed Using Example 1:

| | |
|---|---|
| Reduction from alkaline pH >7 to 7.2 | Parrot Green |
| pH 4.5-4.8 | Purple/mauve |

Example 2: Using Universal pH Indicator

| | Ingredients | Amount/Range |
|---|---|---|
| pH Modifier matrix | Maleic anhydride | 20 gm |
| | Water to hydrolyze into maleic acid | 55 ml |
| | Itaconic acid | 1 gm |
| | Phosphorous acid H3PO3 | 20 gm |
| | Glycine | 4 gm |
| | Hydrolyzed Proteins | 5 gm |
| | Linear alkyl benzene sulfonic acid/ dodecyl benzene sulfonic acid | 1 gm |
| Surfactant | Sodium Lauryl sulfate | 2 gm |
| | Polysorbate Sorbitan monooleate | 2 gm |
| | Organo Silicone surfactant | 6 gm |
| | dioctylsulfosuccinate | 1 gm |
| Penetrator and Solvent for pH Indicators | Methanol/propanol/Ethylene Glycol/Propylene Glycol | 5 ml |
| pH Indicator | Methyl Red | 0.036-0.05 gm |
| | Bromothymol Blue | 0.091-0.20 gm |
| | Thymol Blue | 0.067-0.15 gm |
| | Para Nitro Phenol | 0.25-0.70 gm |
| | Phenolphthalein | 0.036-0.30 gm |
| Thickner | Sodium CMC | 0.05 gm |
| | Guar gum/Xanthan Gum | 0.05 gm |
| | Polyacryl amide | 0.05 gm |
| Water | To make volume | 100 ml |

Step a: Hydrolyzing maleic anhydride into maleic acid by adding maleic anhydride into water and allowing it to hydrolyse by applying heat at 75-80° C. to form maleic acid then adding itaconic acid, phosphorous acid, glycine and hydrolyzed protein subsequently into this solution to make maleic itaconic phosphorous acid amino acid complex.

Step b: To above solution of pH modifier matrix, surfactants, wetting agents such as Organo silicone surfactant, Sorbitan monooleate, Sodium lauryl sulphate, dioctyl sulfosuccinate are added. Natural or artificial thickeners such as guar gum, sodium CMC, xanthum gum, polyacrylates, carbomers are added slowly under stirring maintaining a temp of 65-75° C.

Step c: Preparation of pH indicators solution—pH indicators solution is made separately in separate vessel using solvent for pH indicators and penetrators such as methanol and propanol and using penetrator from glycol series such as monoethylene glycol, propylene glycol by mixing thoroughly all the pH indictors mentioned in the composition.

Step d: adding pH indicator solution containing penetrators and pH indicators solvents to the solution obtained in the step (b) and finally making the volume to 100% by mass using hot demineralised water to obtain the formulation Step e (Optional): The above formulation can also be dried in vacuum or in spray dryer to form dry version of the product and can be converted into granule or tablet form.

The composition of Example 2 when added into hard water having alkaline pH >7.5, the hardness causing salts are complexed and the pH is reduced from alkaline to acidic and the color change is noted as Violet at pH 10.0, Dark Blue pH 9.0, Blue at pH 8.0, Green at pH 7.0 to 7.5, Yellow at pH −6.0, Orange at pH −5.0 and Red at pH 4.0.

Colour Change Noticed Using Example 2:

| | |
|---|---|
| Reduction from alkaline pH 10 | Violet |
| pH 9.0 | Dark Blue |
| pH 8.0 | Blue |
| pH 7.0-7.5 | Green |
| pH 6.2 | Yellow |
| pH 5.0 | Orange |
| pH 4.0 | Reddish Orange |

Example 3: Using Screened Indicator

Color Change: Violet at pH 3.8, Green at pH 4.2 and Yellow at pH −7.2

| | Ingredients | Amount/Range |
|---|---|---|
| pH Modifier matrix | Maleic anhydride | 20 gm |
| | Water to hydrolyze into maleic acid | 55 ml |
| | Itaconic acid | 1 gm |
| | Phosphorous acid H3PO3 | 20 gm |
| | Glycine | 4 gm |
| | Hydrolyzed Proteins | 5 gm |
| | Linear alkyl benzene sulfonic acid/ dodecyl benzene sulfonic acid | 1 gm |
| Surfactant | Sodium Lauryl sulfate | 2 gm |
| | Polysorbate Sorbitan monooleate | 2 gm |
| | Organo Silicone surfactant | 6 gm |
| | dioctylsulfosuccinate | 1 gm |
| Penetrator | Methanol/propanol/Ethylene Glycol/Propylene Glycol/ | 5 ml |
| pH Indicators | Methyl Orange | 0.3 gm |
| | Xylene Cyanol | 0.2 gm |
| | Para Nitro Phenol | 0.3 gm |
| Thickner | Sodium CMC | 0.05 gm |
| | Guar gum/Xanthan Gum | 0.05 gm |
| | Polyacryl amide | 0.05 gm |
| Water | To make volume | 100 ml |

Step a, Step b, Step c and Step d are carried out as per given in Examples 1 and 2. The composition of Example 3 when added into hard water having alkaline pH >7.5, the hardness causing salts are complexed and the pH is reduced from alkaline to acidic and the color change is noted as Violet to green from 3.8 to 4.1.

Colour Change Noticed Using Example 3:

| | |
|---|---|
| Reduction from alkaline pH >7 to 7.2 | Yellow |
| pH 4.2 | Green |
| pH 3.6-3.8 | Violet |

Example 4: Using Congo Red and p-Nitro Phenol as pH Indicator

Congo Red which Changes Color to Blue at pH 3 and Red at pH 5

Second pH indicator p-nitrophenol which becomes colorless at pH 5 and yellow at pH 7.2

| | Ingredients | Amount/Range |
|---|---|---|
| pH Modifier matrix | Maleic anhydride | 20 gm |
| | Water to hydrolyze into maleic acid | 55 ml |
| | Itaconic acid | 1 gm |
| | Phosphorous acid H3PO3 | 20 gm |
| | Glycine | 4 gm |
| | Hydrolyzed Proteins | 5 gm |

-continued

| | Ingredients | Amount/Range | |
|---|---|---|---|
| | Linear alkyl benzene sulfonic acid/ dodecyl benzene sulfonic acid | 1 | gm |
| Surfactant | Sodium Lauryl sulfate | 2 | gm |
| | Polysorbate Sorbitan monooleate | 2 | gm |
| | Organo Silicone surfactant | 6 | gm |
| | dioctylsulfosuccinate | 1 | gm |
| Penetrator & Solvent for pH Indicators | Methanol/propanol/Ethylene Glycol/Propylene Glycol | 5 | ml |
| pH Indicator | Congo Red | 1.5-2.0 | gm |
| | P Nitrophenol | 1.0 | gm |
| Thickener | Sodium CMC | 0.05 | gm |
| | Guar gum/Xanthan Gum | 0.05 | gm |
| | Polyacryl amide | 0.05 | gm |
| Water | To make volume | 100 | ml |

Step a, Step b and Step c are carried out as per given in Examples 1 and 2. The composition of Example 4 when added into hard water having alkaline pH >7, the hardness caused salts to complex and the pH is reduced from alkaline to acidic and the color change noticed using Example 4 is as follows:

| Reduction from alkaline pH >7 to neutral At pH 7.0-6.8 | Yellow |
|---|---|
| pH 5.0 | Reddish |
| pH 3.0 to 3.5 | Bluish Violet |

Example 5: A Multifunctional Chemical Composition of the Present Invention is Also Prepared as TWIN PACK Consisting 2 Different Packs as Following

| First pH Modifier pack containing | pH modifier complex with surfactants in liquid, paste, granulate, solid powder, tablet form |
|---|---|
| Second pH Indicator pack Consisting | pH indicators with solvents for pH indicators, penetrator, thickener and other auxiliary chemicals in Liquid, paste, granulate, solid powder, tablet form. |

The first pack consists of pH modifier complex along with surfactants with the quantity of water added so as to form 80 parts by volume of the composition selected from any one from Examples No 1 to 4 mentioned above, whereas the second pack consists pH indicator pack consists of pH indicators, Solvents for pH indicators, penetrators, thickener, water. The water will be added so as to form remaining 20 parts by volume.

Above mentioned both the packs can be dried using suitable dryer to form powder, granule and is also be converted into tablet or pellet form using suitable tableting or pelleting machinery.

Application:—

While using Twin pack of the multifunctional nutritional adjuvant, first small quantity of first Pack consisting pH modifier complex with surfactants is added to water for treatment at the rate of 0.5 ml per ltr. of water in order to reduce the pH of water. Then the second pack consisting pH indicator, solvents for pH indicator, penetrators, thickeners is added at 0.2 ml/ltr of water to check the reduction achieved in the pH of water which will be shown by the color achieved to the treated water after addition of the composition of second pack and if the desired pH is not achieved then slowly the composition from first pack is added so as to achieve the desired pH of water. Composition from second Pack is added if the color of the treated water is not clearly visible.

Application of Invention with Various Agrochemicals

Example 6: Use with Plant Growth Hormones

The composition prepared according to Example 1 is used along with the Gibberellic acid (GA), a plant growth hormone, which is having half-life of few minutes in alkaline water. The composition of invention as described in Example 1 is added to 100 lit. borewell water having TDS of 1500 ppm till the pH of the water is reduced to 4.0 to 5.0 which is indicated by purple color imparted to the water.

This treated water using the chemical prepared as per Example 1 after achieving the desired pH of water is used to prepare 36 ppm of GA solution which is further used for dipping of grape bunches.

In untreated/control trial the 45 ppm of GA solution is prepared using same borewell water having 1500 ppm. Herein control, the composition of the Example 1 or 2 is not added in borewell water.

Treatment:—WATER+Multifunctional composition+Gibbrellic acid 36 ppm

Control:—WATER+Gibbrellic acid 45 ppm

This treatment was done 3 times at different stages of grape development such capfall, 2 times during berry development stage.

Effect of Use of Various Compositions of Invention Along with Gibbrrellic Acid (GA) on Grapes:—

The well water having alkaline pH 7.65 is used for making GA solution for dipping of grapes.

In treatment the compositions of agrochemical GA as per given in invention are used.

The results are tabulated as following:

| Treatment | GA Conc. in dipping solution | pH of GA dipping solution | Color of treated water before addition of GA | Weight of berry (gm) | Weight of Bunch (Gm) | Yield/ Vine (Kg) | Total Soluble solids (TSS) % Brix | % Increase over Control | Saving of GA over Control |
|---|---|---|---|---|---|---|---|---|---|
| Control | 45 ppm | 7.65 | Colorless | 2.67 | 285.3 | 8.17 | 18.73 | — | 0% |
| Composition of Example 2 | 36 ppm | 5.0 | Orange | 2.88 | 371.20 | 11.52 | 20.56 | 9.77% | 20% |
| Composition of Example 1 | 36 ppm | 4.2 | Purple | 3.30 | 436.66 | 14.66 | 22.23 | 18.68% | 20% |

Example 7: Use with Herbicide Glyfosate on Weeds in Cotton Crop

| Treatment | Dosage of Glyfosate | pH of Glyfosate spray solution | Color of treated water before addition of Glyfosate | Control of weeds | % Increase over Control |
|---|---|---|---|---|---|
| Control | 1 Ltr/acre | 7.50 | Colorless | 72% | — |
| Composition of Example 1 | 850 ml/acre | 4.2 | Purple | 96% | 33% |
| Composition of Example 4 | 800 ml/acre | 3.50 | Bluish Violet | 93% | 29% |

Example 8: Use with Cypermethrin on Tomato

Tomato crop infested with worms is sprayed with Cypermethrin 25% EC using normal well water and well water treated with the compositions of the invention. One acre is treated only with water and another 2 acre plot is treated with composition of the invention. In both the plots, pest is controlled. In treated plot, the pest control is achieved at 95% and with 15% saving in the dosage of cypermethrin pesticide.

Further, it is noted that in 2 acre treated plot the fungal attack was very less and only 1 round of fungicide is required, whereas in 1 acre control plot, 2 rounds of fungicides are used in order to control the fungal attack.

This shows that the use of novel multifunctional nutritional chemical composition of the present invention, increases the systemic resistance of plants towards fungus.

| Treatment | Dosage of Cypermethrin | pH of Cypermethrin Spray solution | Color of treated water before addition of Glyfosate | Control of Pest worms | % Saving of Insecticide Control |
|---|---|---|---|---|---|
| Control | 150 ml/acre | 7.20 | Colorless | 90% | 0% |
| Composition of Example 1 | 125 ml/acre | 4.5 | Purple | 95% | 15% |

I claim:

1. A multifunctional nutritional adjuvant chemical composition comprising:
   i. a pH modifying complex matrix comprising a) plant nutrients, b) phosphorous acid, and c) a mixture of itaconic acid, wherein said itaconic acid is unsaturated; and maleic acid,
   ii. a pH indicator,
   iii. a surfactant,
   iv. a penetrating agent,
   v. an auxiliary chemical; and
   vi. a solvent,
      diluted in water;
   wherein said composition reduces the usage of agrochemicals by reducing the hydrolysis of agrochemicals and effectively increasing their efficiency.

2. The multifunctional nutritional adjuvant chemical composition as claimed in claim 1, wherein said pH modifying complex matrix further comprises:
   an amino acid,
   hydrolyzed protein, and
   a linear alkyl benzene sulfonic acid.

3. The multifunctional nutritional adjuvant chemical composition as claimed in claim 2, wherein said pH modifying complex matrix is present in an amount of 45-55% by volume of the composition.

4. The multifunctional nutritional adjuvant chemical composition as claimed in claim 1, wherein said pH indicator is selected from the group consisting of methyl red, para and ortho nitrophenol, methylene blue, congo red, bromothymol blue, thymol blue, phenolphthalein, methyl orange, xylene cyanol, neutral red, napthyl red, bromocresol purle, bromo xylenol blue, bromocresol green, alizarin red, ortho cresol red, resazurin and 2,4-dinitrophenol.

5. The multifunctional nutritional adjuvant chemical composition as claimed in claim 4, wherein said pH indicator is present in an amount of 0.8 to 3.0% by volume of the composition.

6. The multifunctional nutritional adjuvant chemical composition as claimed in claim 1, wherein said surfactant is selected from the group consisting of an organo silicone based surfactant compound, sorbitan mono oleate, sodium lauryl sulfate and dioctylsulfosuccinate sodium salt.

7. The multifunctional nutritional adjuvant chemical composition as claimed in claim 6, wherein said surfactant is present in an amount of 8 to 15% by volume of the composition.

8. The multifunctional nutritional adjuvant chemical composition as claimed in claim 1, wherein said penetrating agent and said solvent are selected from the group consisting of propanol, methanol, ethylene glycol/propylene glycol.

9. The multifunctional nutritional adjuvant chemical composition as claimed in claim 8, wherein said penetrating agent and said solvent are present in an amount of 5 to 10% by volume of the composition.

10. The multifunctional nutritional adjuvant chemical composition as claimed in claim 1, wherein said auxiliary chemical is selected from the group consisting of a thickener, an antifoaming agent, a defoamer, a humectant, a stabilizer, and a mixture thereof.

11. The multifunctional nutritional adjuvant chemical composition as claimed in claim 1, wherein said composition is a liquid, a gel, a paste, a powder, a granule, a tablet, or a pellet.

12. A process for preparation of a multifunctional nutritional adjuvant chemical composition, which comprises, a) hydrolyzing maleic anhydride into maleic acid by adding maleic anhydride into water followed by allowing it to hydrolyse by applying heat at 75-80° C. to form maleic acid;
b) adding itaconic acid, phosphorous acid, glycine and hydrolyzed proteins subsequently into the maleic acid solution of step (a) to obtain pH modifier matrix;
c) slowly adding surfactants/wetting agents, natural or artificial thickeners to the solution obtained in step (b) under stirring and maintaining the temp. at 65-75° C.;
d) preparing a pH indicator solution using penetrators and pH indicator solvents;
e) adding pH indicator solution of step (d) to the solution obtained in the step (c) and finally making the volume to 100% by mass using hot demineralised water to obtain the formulation;
f) optionally, drying the formulation of step (e) in vacuum or in spray dryer to form dry version of the final product followed by converting into granule or tablet or pellet form.

13. A method of providing nutrient supplement to plants by mixing a multifunctional nutritional adjuvant chemical composition as claimed in claim 1, with hard water to obtain a composition having an acidic pH; and
administering the composition having an acidic pH to the plants.

14. A pH modifying complex matrix for use in agriculture, comprising:
a mixture of maleic anhydride and itaconic acid,
phosphorous acid,
an amino acid,
hydrolyzed protein,
a linear alkyl benzene sulfonic acid, and
water in an amount effective to hydrolyze said maleic anhydride into maleic acid.

15. The pH modifying complex matrix of claim 14, comprising, based on volume of the composition:
15 to 25% by volume maleic anhydride,
1 to 3% by volume itaconic acid,
15 to 25% by volume phosphorous acid,
4 to 6% by volume an amino acid,
4 to 8% by volume hydrolyzed protein,
1 to 3% by volume a linear alkyl benzene sulfonic acid, and
water in an amount effective to hydrolyze said maleic anhydride into maleic acid.

16. An agricultural composition comprising:
the pH modifying complex matrix of claim 14,
a pH indicator,
a surfactant,
a penetrating agent,
an auxiliary chemical,
a solvent, and
a hydrolysable agrochemical,
said agricultural composition being diluted in water for use in agriculture,
wherein said agricultural composition increases the efficiency of said hydrolysable agrochemical by reducing hydrolysis of said hydrolysable agrochemical.

17. The agricultural composition of claim 16, wherein said agricultural composition comprises from 45% to 55% by volume of said pH modifying complex matrix.

18. The agricultural composition of claim 16, wherein said pH indicator is selected from the group consisting of methyl red, para and ortho nitrophenol, methylene blue, congo red, bromothymol blue, thymol blue, phenolphthalein, methyl orange, xylene cyanol, neutral red, napthyl red, bromocresol purle, bromo xylenol blue, bromocresol green, alizarin red, ortho cresol red, resazurin and 2,4-dinitro phenol.

19. The agricultural composition as claimed in claim 16, wherein said penetrating agent and said solvent are selected from the group consisting of propanol, methanol, ethylene glycol, propylene glycol, and mixtures thereof.

20. The agricultural composition as claimed in claim 16, wherein said auxiliary chemical is selected from the group consisting of thickeners, antifoaming agents, defoamers, humectants, stabilizer, and mixtures thereof.

21. A binary nutritional adjuvant chemical composition, comprising a first component and a second component;
said first component comprising the pH modifying complex matrix of claim 14 and a surfactant; and
said second component comprising a pH indicator, a penetrating agent, an auxiliary chemical, and a solvent.

* * * * *